US012806408B2

(12) United States Patent
Shin et al.

(10) Patent No.: US 12,806,408 B2
(45) Date of Patent: Nov. 24, 2026

(54) SMART WEARABLE WRISTBAND WITH ELECTRICAL ELECTRODES FOR NON-INVASIVE NEUROSTIMULATION AND NON-INVASIVE HIGH BLOOD PRESSURE RELIEF SYSTEM

(71) Applicant: D-TRIPLE CO., LTD., Gumi-si (KR)

(72) Inventors: Hyeon Sik Shin, Gimcheon-si (KR); Jun Ho Hong, Gumi-si (KR); Hong Beom Park, Gumi-si (KR); Jae Kyung Ha, Waegwan-eup (KR)

(73) Assignee: PRONOID Co., Ltd., Gumi-si (KR)

( * ) Notice: Subject to any disclaimer, the term of this patent is extended or adjusted under 35 U.S.C. 154(b) by 69 days.

(21) Appl. No.: 18/813,278

(22) Filed: Aug. 23, 2024

(65) Prior Publication Data

US 2024/0408382 A1 Dec. 12, 2024

Related U.S. Application Data

(63) Continuation-in-part of application No. PCT/KR2022/012666, filed on Aug. 24, 2022.

(30) Foreign Application Priority Data

Feb. 25, 2022 (KR) ........................ 10-2022-0024780

(51) Int. Cl.
*A61N 1/04* (2006.01)
*A61N 1/36* (2006.01)
*A61N 5/06* (2006.01)

(52) U.S. Cl.
CPC ......... *A61N 1/0472* (2013.01); *A61N 1/0456* (2013.01); *A61N 1/36031* (2017.08); *A61N 5/0613* (2013.01); *A61N 2005/0651* (2013.01); *A61N 2005/066* (2013.01)

(58) Field of Classification Search
CPC .... A61N 1/0472; A61N 1/0476; A61N 1/048; A61N 1/36031; A61N 1/36034; A61N 1/0456; A61N 1/0452; A61N 5/0613; A61N 5/0619; A61N 5/0618; A61N 5/062; A61N 2005/0651; A61N 2005/066
USPC ............................................................ 607/3
See application file for complete search history.

(56) References Cited

U.S. PATENT DOCUMENTS

2021/0052221 A1* 2/2021 Panneer Selvam ... A61B 5/1117

FOREIGN PATENT DOCUMENTS

JP 2019-523031 A 8/2019
KR 10-2010-0072993 A 7/2010

OTHER PUBLICATIONS

International Search Report, PCT/KR2022/012666, Nov. 28, 2022.

* cited by examiner

*Primary Examiner* — Aaron F Roane
(74) *Attorney, Agent, or Firm* — Quantum Patent Law Firm; Seongyoune Kang

(57) ABSTRACT

The present invention relates to a smart wearable wristband with electrical electrodes for non-invasive neurostimulation, comprising: a main unit for fitting around a wrist and measuring user's vital signs; and a stimulation portion for stimulating median nerve or ulnar nerve located below Neiguan PC 6 or JianShi PC 5. According to the present invention, hypertension or stress can be effectively alleviated.

11 Claims, 12 Drawing Sheets

SMART WEARABLE WRISTBAND WITH ELECTRICAL ELECTRODES FOR NON-INVASIVE NEUROSTIMULATION AND NON-INVASIVE HIGH BLOOD PRESSURE RELIEF SYSTEM

CROSS-REFERENCE TO RELATED APPLICATIONS

This patent application is a continuation-in-part of PCT/KR2022/012666, filed Aug. 24, 2022 and the entire contents of which are incorporated herein by reference, which claims priority to Korean Patent Application No. 10-2022-0024780, filed Feb. 25, 2022 and the entire contents of which are incorporated herein by reference.

FIELD OF THE INVENTION

The present invention relates to a smart wearable wristband equipped with electrical electrodes for non-invasive neurostimulation. More specifically, it concerns a wristband designed to stimulate the wrist nerves with low-frequency electrical impulses, thereby aiding in user relaxation. This work was supported by the Korea Medical Device Development Fund grant funded by the Korea government (the Ministry of Science and ICT, the Ministry of Trade, Industry and Energy, the Ministry of Health & Welfare, the Ministry of Food and Drug Safety) (Project Number 1711196543, RS-2023-00253560).

BACKGROUND

With the recent proliferation of smartphones and wearable devices, there has been increased attention on health metric measurement. Traditionally, these applications have primarily involved using accelerometer sensors to measure steps and activity levels, or heart rate sensors for monitoring cardiac rates. However, there has been a growing interest in leveraging ECG sensors to monitor medically significant indicators, including arrhythmia, blood pressure, and blood glucose levels.

To facilitate real-time monitoring of these vital signs, wearable devices are designed to be worn on the wrist and portable. By integrating with medical technology, these devices can utilize the measured vital signs to monitor or diagnose a user's physical condition.

Recent medical journals have reported that changes in vital signs, such as heart rate, occur when individuals experience stress or excitement. It has been demonstrated that these conditions can be quantified and managed by using the vital sign data collected from wristbands.

Additionally, recent advances in traditional Chinese medicine suggest that non-invasive electrical stimulation can stabilize vital signs under stress. Moreover, numerous efforts are underway to treat various conditions, including hypertension, using non-invasive electrical stimulation methods. These approaches for stress relief and other treatments could offer significant benefits if integrated into wearable devices, allowing for continuous verification of their effectiveness through vital sign monitoring. However, the inadequate technological development in wearable devices has hindered their practical implementation.

Furthermore, although many smart wristbands on the market are capable of analyzing stress and excitement through vital sign measurements, none include a device for delivering electrical stimulation. This necessitates the use of separate modules, leading to the inconvenience of carrying multiple devices.

PRIOR ART REFERENCE

Korean Patent Registration No. 10-2335766

SUMMARY OF THE INVENTION

To address the aforementioned issues, the object of this invention is to provide a smart wearable wristband equipped with electrical electrodes for non-invasive neurostimulation. This wristband allows for the application of electrical stimulation to alleviate symptoms or conditions based on stress and excitability states measured through biosignal measurements.

Another object of this invention is to provide a smart wearable wristband with electrical electrodes for non-invasive neurostimulation that allows for the modification or adjustment of the site of electrical stimulation on the wrist. This enables stimulation of various acupuncture points from a Chinese medicine perspective.

A further object of this invention is to provide a smart wearable wristband with integrated electrical stimulation modules. This feature enhances portability and enables application of easy electrostimulation outdoors, thereby stabilizing the user's vital signs.

Additionally, another object of this invention is to provide a non-invasive system for relieving hypertension and stress. This system analyzes physical information collected from a wearable device to obtain physical and blood pressure history information. Based on this data, it calculates stimulation information to provide electrical stimulation, vibration, far infrared light, or near infrared light to at least one JianShi PC 5 or Neiguan PC 6 of the user, effectively alleviating hypertension or stress.

Solution to the Challenge

To address the aforementioned purpose, the present invention provides a smart wearable wristband with electrical electrodes for non-invasive neurostimulation, comprising: a main unit for fitting around a wrist and measuring user's vital signs; and a stimulation portion for stimulating median nerve or ulnar nerve located below Neiguan PC 6 or JianShi PC 5.

In this case, the smart wearable wristband may further comprises a stimulation band formed at one end of the main unit, electrically connected to the main unit for receiving power, and having a fixing ring at the other end; and a retaining band formed on another end of the main unit, coupled to the stimulation band via a fastening end, securing the main unit and the stimulation band to user's wrist; wherein the stimulation portion positioned on the outer surface of the stimulation band and receives power from the stimulation band.

Further, the stimulation band may comprises a flexible printed circuit board (FPCB) having a pogo pin at one end of the FPCB, electrified holes for supplying power to the stimulation portion, and through-holes formed at a predetermined interval for insertion of the fastening end; a fixture for wrapping around to protect the pogo pin, and engaging with the main unit to prevent separation; and a housing accommodating the FPCB and having connection holes and fastening holes formed at the predetermined intervals at the same locations as the through-holes and allowing the electrified holes to be exposed for connection with the stimulation portion, wherein the stimulation portion is coupled to the connection holes and the electrified holes on the stimulation band, allowing stimulation position to be changed.

Further, the FPCB may be configured to bend to conform to the wrist and the stimulation portion controls intensity and timing of stimulation based on the vital signs.

Further, the stimulation portion may comprise a body formed to wrap around the stimulation band, the body being configured to slide along the stimulation band; and electrode ends formed on the lower surface of the body, the electrode ends being electrically connected to supply positive and negative charge when inserted into said stimulation band and being in contact with the wrist to provide electrical stimulation.

Further, the stimulation portion is configured to slidably move along said stimulation band to adjust neurostimulation portion.

Further, a plurality of stimulation portions may be provided for simultaneous stimulation at multiple locations on the wrist.

Meanwhile, the present invention also provides a non-invasive hypertension or stress relief system comprising: a user terminal; an AI analysis server; a hypertension and stress reliever; and a wearable device worn on a user to collect physical information about the user, wherein the user terminal transmits the physical information to the AI analysis server, and the AI analysis server generates physical analysis data based on user's physical information and blood pressure history; calculates stimulation information based on the physical analysis; and transmits the stimulation information to the user terminal; and wherein the hypertension and stress reliever provides electrical stimulation in accordance with the stimulation information and to stimulates median nerve or ulnar nerve below the Neiguan PC 6 or JianShi PC 5.

In this case, the hypertension and stress reliever further provides vibration stimulation or light stimulation in accordance with the stimulation information.

Further, the user terminal comprises: a smartphone communication unit communicating with the wearable device, the hypertension and stress reliever and the AI analysis server, transmitting the physical information to the AI analysis server and receiving the stimulation information; an input unit allowing manual input of physical information by the user, and querying of the physical analysis data, the blood pressure history, and the stimulation information; an adjustment unit for controlling the transmission of said stimulation information from said smartphone communication unit to a smartphone receiver and a smartphone transmitter sends the stimulation information to the hypertension and stress reliever.

Further, the AI analysis server may comprise: a server communication unit for wirelessly communicating with the smartphone communication unit to receive physical information; an AI analysis unit for analyzing the physical information to generate physical analysis information and blood pressure history, comparing preset analysis information with the received information, and determining if there is an emergency; a data management unit for storing and managing the physical analysis information and blood pressure history; and a stimulation information calculation unit for calculating the stimulation information based on the physical analysis and blood pressure history, wherein the server communication unit transmits the stimulation information to the smartphone communication unit.

Further, the hypertension and stress reliever may include: a strap connector; a pair of straps attached to either side of said strap connector; a stimulation information receiving unit for receiving the stimulation information from the smartphone communication unit; a stimulation generating unit for generating an electrical stimulation waveform based on the stimulation information; a stimulation portion coupled to said strap connection providing electrical, vibration, and light stimulation to at least a part of the user's arm according to the stimulation information.

The non-invasive hypertension or stress relief system may further comprises a plurality of near-infrared LEDs for generating near-infrared light according to the stimulation information and irradiating said light into the user's blood vessels.

In this case, the non-invasive hypertension or stress relief system may further comprise: a silicone pad disposed adjacent to the plurality of near-infrared LEDs, generating far-infrared light by heating and irradiating the far-infrared light into user's blood vessels.

The effects of the invention are not limited to the above effects, but are to be understood to include all effects that can be inferred from the detailed description of the invention or from the composition of the invention as recited in the claims.

DETAILED DESCRIPTION OF THE PREFERRED EMBODIMENT

Figure 1:
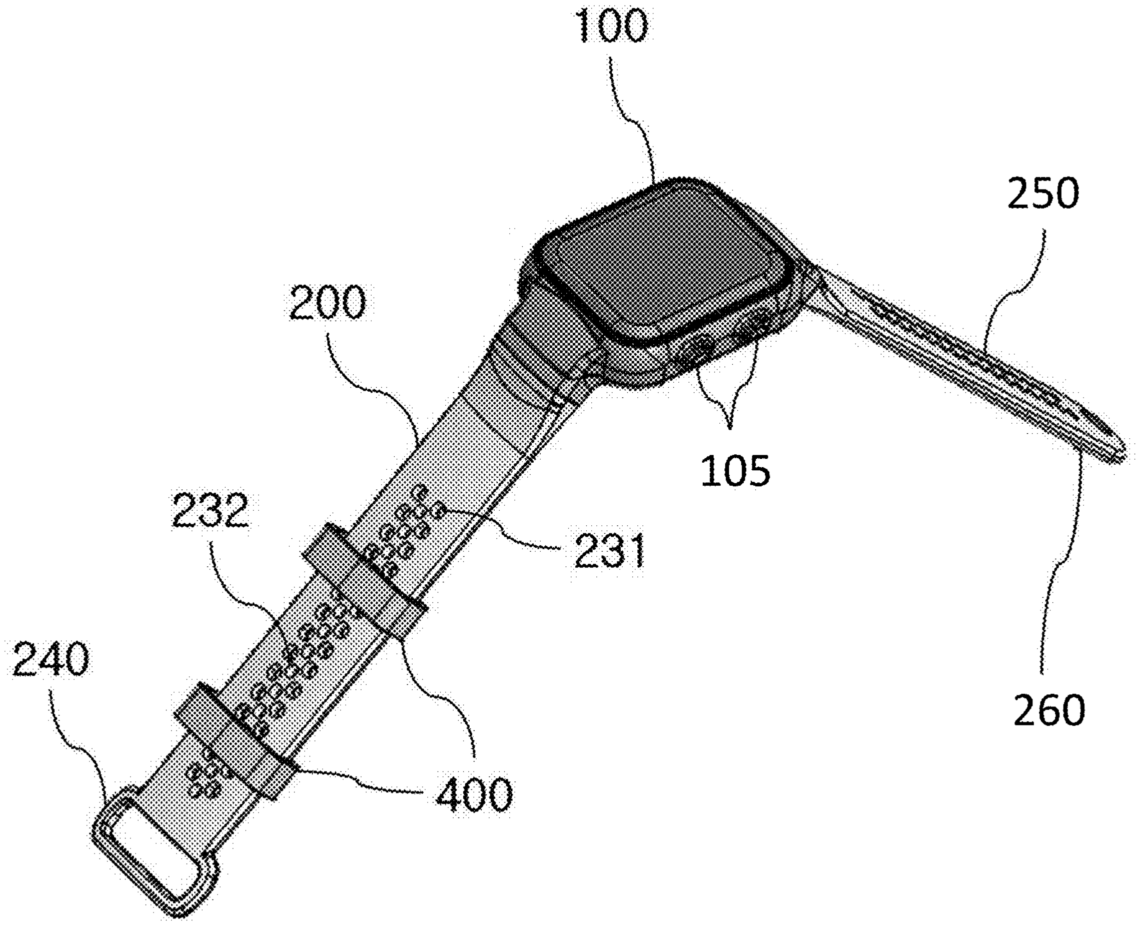
FIG. 1 is a perspective view illustrating the appearance of a smart wearable wristband with electrical electrodes for non-invasive neurostimulation, according to the present invention.

The present invention will be described hereinafter with reference to the accompanying drawings. However, it should be noted that the invention can be implemented in various forms and is not limited to the embodiments described herein. For clarity in the drawings, parts unrelated to the description have been omitted, and similar elements throughout the specification are marked with corresponding reference numerals.

Throughout this specification, when a part is said to be 'connected' to another part, this encompasses both 'direct connections' and 'indirect connections' where other elements may intervene. Moreover, when a part is said to 'include' a component, unless explicitly stated otherwise, it implies the possibility of additional components, not the exclusion of them.

The terms used in this specification are intended to describe specific embodiments only, not to limit the invention. Unless contextually evident, singular expressions include their plural forms. Here, terms like 'comprises' or 'includes,' and similar expressions, indicate the presence of stated features, numbers, steps, operations, components, parts, or their combinations, and should not be construed as excluding the possibility of one or more additional features, numbers, steps, operations, components, parts, or combinations thereof.

Hereinafter, a preferred embodiment of the invention will be described in detail, with reference to the attached drawings.

Figure 2:
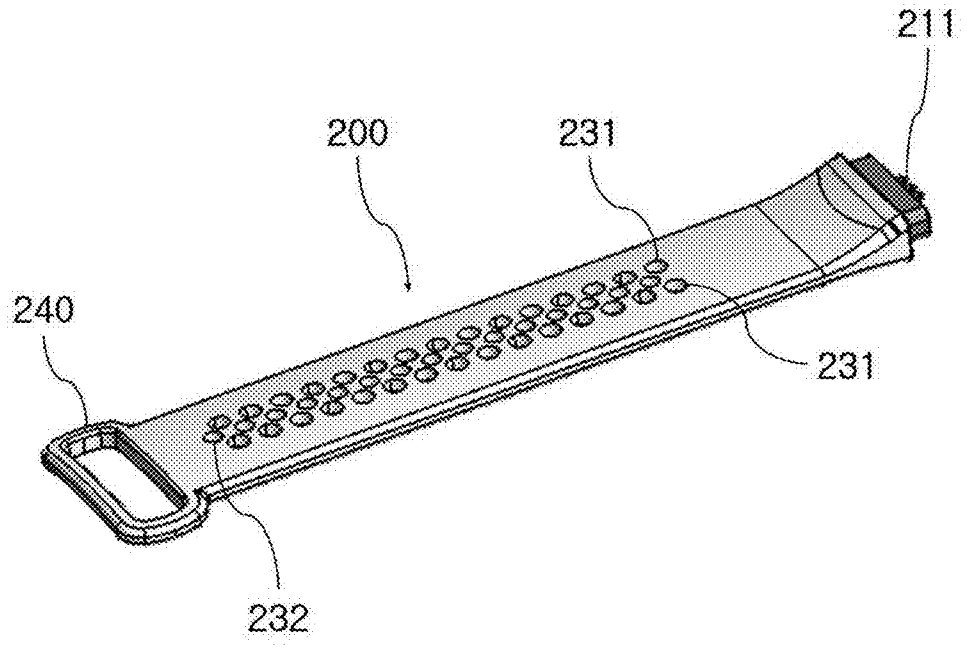
FIG. 2 is a perspective view showing the stimulation band of a smart wearable wristband with electrical electrodes for non-invasive neurostimulation, as per the present invention.
Figure 3:
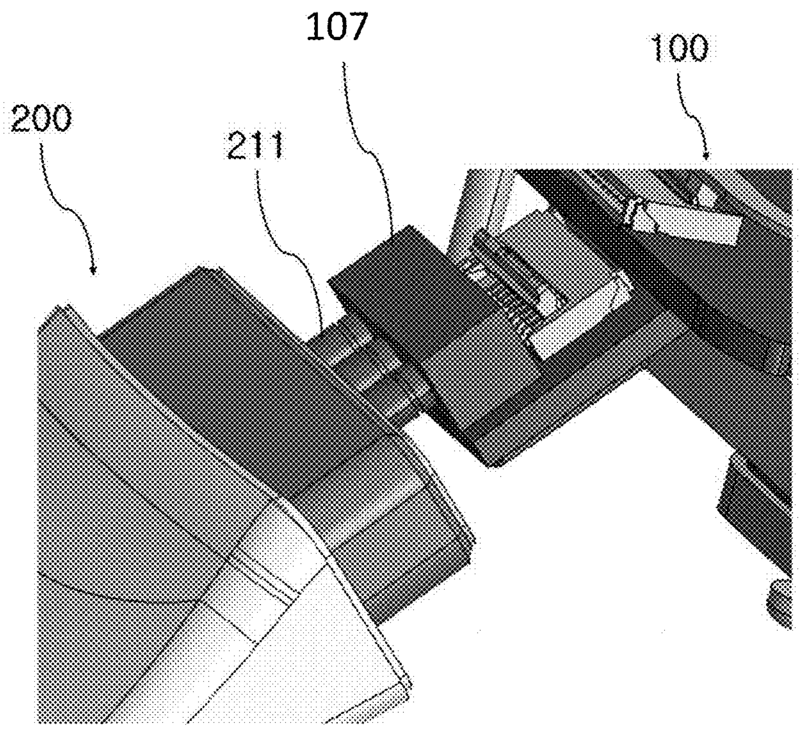
FIG. 3 is an enlarged view of the stimulation band and body portion of a smart wearable wristband, which includes electrical electrodes for non-invasive neurostimulation, according to the present invention.

FIG. 1 is a perspective view illustrating the appearance of a smart wearable wristband with electrical electrodes for non-invasive neurostimulation, according to the present invention. FIG. 2 is a perspective view showing the stimulation band 200 of a smart wearable wristband with electrical electrodes for non-invasive neurostimulation, as per the present invention. FIG. 3 is an enlarged view of the stimulation band 200 and main unit 100 of a smart wearable wristband, which includes electrical electrodes for non-invasive neurostimulation, according to the present invention.

As shown in FIGS. 1 to 3, a smart wearable wristband with electrical electrodes for non-invasive neurostimulation according to the present invention includes: a main unit 100 formed to fit closely to a wrist to measure a user's vital signs in real time for diagnosis; a stimulation band 200 attached on one side of the main unit 100 and electrically connected to the main unit 100 to receive power; and a securing band 250 attached on the other side of the main unit 100 and coupled to the stimulation band 200 to secure the main unit 100 and the stimulation band 200; and a stimulation portion 400 formed to be positionable on the stimulation band 200 and powered by the stimulation band 200 to stimulate nerves in the wrist area.

The main unit 100 may include a sensor part on the lower surface to measure the user's vital signs, and the sensor part enables the user's biometric information, stress state, and excitement state to be grasped.

The main unit 100 may have a communication module for communicating with an external smart device, a battery for supplying power, and a control module for diagnosing a user's condition and prescribing electrical stimulation based on information acquired through the sensor part, and, if necessary, the upper surface of the main unit 100 is formed as a display so that the operating status can be checked.

In addition, a plurality of control buttons 105 are provided on the side of the main unit 100 to control or operate the operation of the main unit 100, and a charging terminal or a wireless charging module is formed to supply external power to the battery.

It can be, but is not limited to, a rectangular shape, but can also be a circle or a square with rounded corners.

Furthermore, to ensure that the main unit 100 remains closely fitted to the wrist, stimulation band 200 and securing band 250 are attached to both sides of the main unit 100. Each band wraps around opposite sides of the wrist and then overlaps and secures together, effectively holding the main unit 100 in place on the wrist.

The stimulation band 200 may have pogo pins 211 formed thereon for engagement with the connection terminal 107 formed on one side of the main unit 100, and the pogo pins 211 are electrically connected to the main unit 100 by contacting the connection terminal 107, thereby enabling the main unit 100 to receive power from a battery formed inside the main unit 100.

Furthermore, the stimulation band 200 has a plurality of fastening holes 232 formed at regular intervals in the center from one end to the other end, and a loop-shaped fastening loop 240 is formed at the other end of the stimulation band 200 into which a securing band 250 can be inserted.

The fastening holes 232 are used to insert the fastening end 260 formed at the end of the securing band 250 to secure the securing band 250 to the top of the stimulation band 200, and the fastening loop 240 is used to allow the securing band 250 to be inserted inwardly so that the securing band 250 does not swing from side to side once it is engaged in the fastening hole 232.

The securing band 250 is attached on the other side of the main unit 100 and is used in conjunction with the stimulus band 200 to secure the main unit 100 closely to the wrist, and has a downwardly protruding fastening end 260 that can be inserted into the fastening hole 232 of the stimulation band 200 to keep the main unit 100 and the stimulation band 200 wrapped around the wrist.

In this case, the securing band 250 may be configured as the same as the stimulation band 200, if necessary, with the fastening loop 240 changed to the fastening end 260, in which case the stimulation portion 400 may also be positioned on the securing band 250 to provide electrical stimulation.

The stimulation portion 400 may be formed in the form of a ring that wraps around the outer surface of the stimulation band 200 so that it can be moved along the outer surface of the stimulation band 200 in one direction or the other, and the lower surface is formed to stimulate the nerve based on the power supplied from the stimulation band 200, so that the nerve can be stimulated according to the state of the user to relieve muscle tension by stimulating the nerve with electricity according to the state of stress or excitement.

Figure 12A:
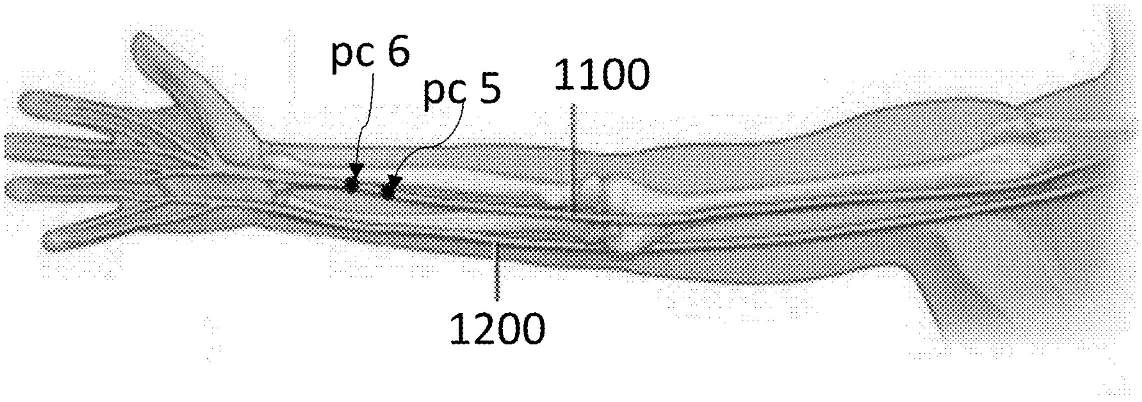
FIGS. 12A and 12B are diagrams illustrating a non-invasive neurostimulated arm part according to one embodiment of the present invention.
Figure 12B:
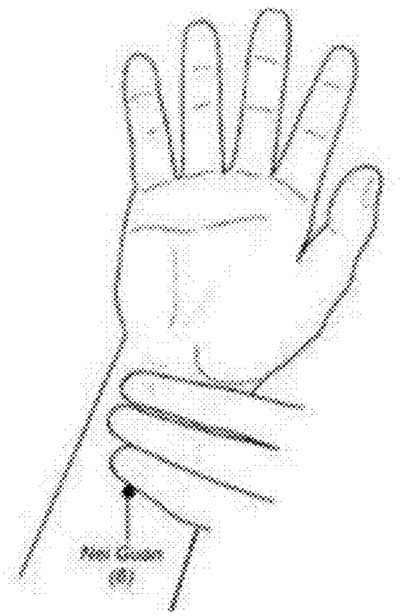

As described herein, the Neiguan PC 6 and the JianShi PC 5 are acupuncture points located on the inner side of the arm (where the inner side refers to the direction of the palm of the hand). The Neiguan PC 6 is located approximately three fingers' breadth from the wrist crease (see FIG. 12B), while the JianShi PC 5 is situated 3 cm towards the shoulder from the Neiguan PC 6. Moreover, 'proximal' in this context refers to points within a distance of 1 cm or less from either the Neiguan PC 6 or the JianShi PC 5.

Meanwhile, the stimulation portion 400 can electrically stimulate the median nerve 1100 or ulnar nerve 1200 located below the Neiguan PC 6 or the JianShi PC 5 by passing current. By targeting these nerves, this invention can effectively help in managing hypertension and alleviating stress.

Furthermore, the stimulation portion 400 is designed to accommodate the end of the securing band 250 inserted through the fastening loop 240, thus preventing lateral movement of the securing band 250. Details on how the stimulation portion 400 stimulates the wrist nerves will be discussed later with reference to the attached FIG. 6.

Figure 4:
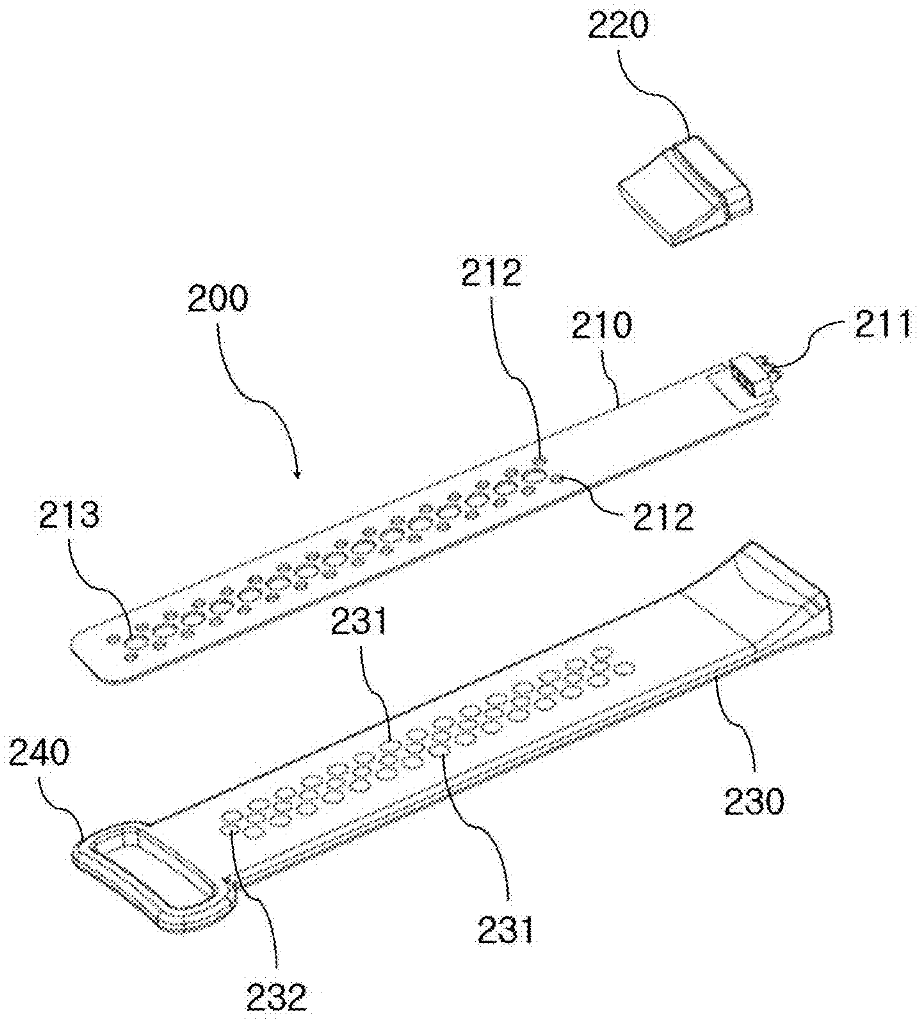
FIG. 4 is an assembly diagram illustrating the stimulation band structure of a smart wearable wristband with electrical electrodes for non-invasive neurostimulation, according to the present invention.
Figure 5:
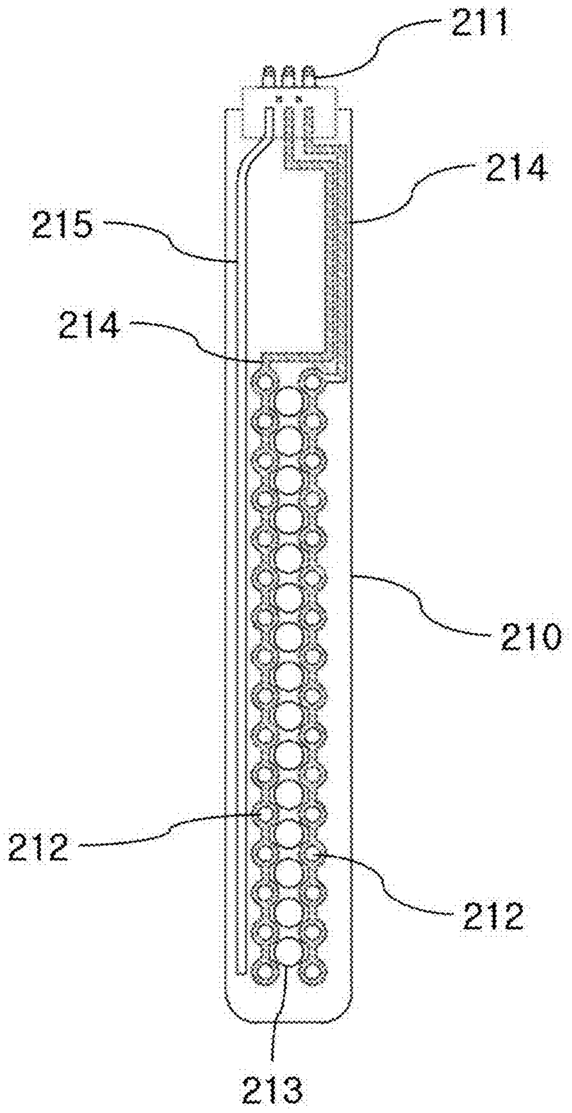
FIG. 5 is a plan view illustrating the FPCB structure of a smart wearable wristband with electrical electrodes for non-invasive neurostimulation, in accordance with the present invention.
Figure 6:
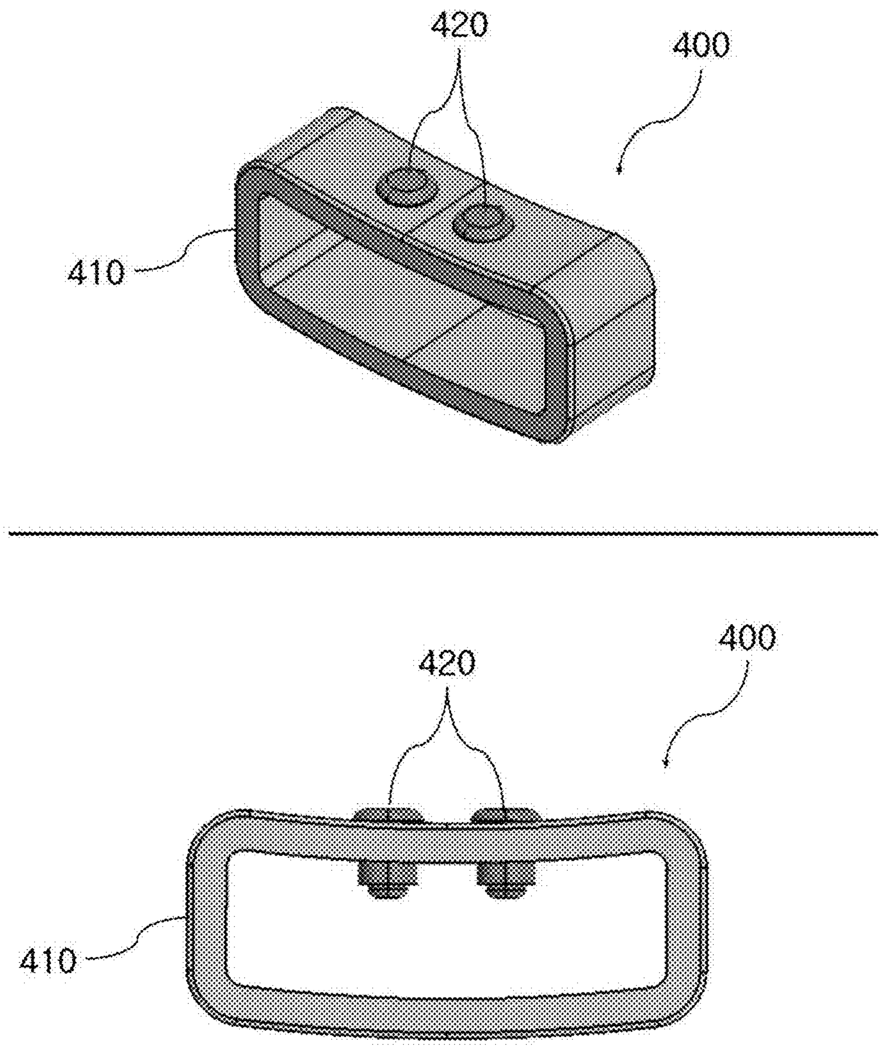
FIG. 6 is a bottom perspective view showing the appearance of the stimulation portion of a smart wearable wristband with electrical electrodes for non-invasive neurostimulation, according to the present invention.

FIG. 4 is an assembly view showing the structure of a stimulation band 200 in a smart wearable wristband equipped with electrical electrodes for non-invasive neurostimulation, according to the present invention. FIG. 5 is a top view showing the structure of an FPCB 210 in a smart wearable wristband with electrical electrodes for non-invasive neurostimulation, according to the present invention. FIG. 6 is a bottom view showing the appearance of a stimulation portion 400 in a smart wearable wristband with electrical electrodes for non-invasive neurostimulation, according to the present invention.

As depicted in FIGS. 4 to 6, the stimulation portion 400 includes a stimulation band 200 consisting of: a FPCB 210 equipped with pogo pins 211 at one end for connecting to the main unit 100, and a pair of electrified holes 212 positioned at regular intervals to supply power across the FPCB 210 from one end to the other. Additionally, a fixture 220 is located at one end of the FPCB 210 to encase and protect the exterior of the pogo pins 211 and to prevent detachment when connected to the main unit 100. There is also a housing 230 with an opening on one side to accommodate the FPCB 210, featuring connection holes 231 aligned with the electrified holes 212 at regular intervals, allowing the electrified holes 212 to be exposed externally and connect to the stimulation site 400 shown in FIG. 6.

The FPCB 210 is further characterized by the housing 230, which is designed to bend or flex to fit the contour of the wrist. This flexibility allows the intensity and timing of the stimulation provided by the stimulation portion 400 to be adjusted based on the vital sign data collected by the main unit 100.

The stimulation portion 400 features a body 410 designed with openings at the front and back, allowing it to encircle and slide along the outer surface of the stimulation band 200. Additionally, a pair of electrode ends 420 are situated on either side of lower surface of the body 410. One side of these electrodes connects electrically to supply positive and negative charge when inserted into the stimulation band 200, while the other side contacts the wrist to deliver electrical stimulation.

The stimulation band 200 is designed to connect to the battery in the main unit 100 shown in FIG. 1 for power and has an FPCB 210, a fixture 220, and a housing 230. These components function to operate the stimulation portion 400 in response to control signals from the control module, facilitating nerve stimulation.

The FPCB 210 is a substrate crafted from flexible material, designed to easily conform to the user's wrist shape. It integrates various electronic components that regulate the operation of the electrical stimulus based on signals from the control module.

At one end of the FPCB 210, multiple pogo pins 211 are installed to establish electrical connections with the connection terminals 107 on the main unit 100. Each pogo pin 211 is connected to a power lines 214 and a control line 215, both of which are integrated into the FPCB 210.

In the case of the power lines 214, the + and − electrode wires are separately formed to allow the stimulation portion 400 to apply electrical stimulation, and the control wire 215 can be used to control the intensity, stimulation time interval for electrical stimulation.

The FPCB 210 also has a plurality of through-holes 213 in the center from one end to the other, the through-holes 213 being formed to allow the fastening end 260 formed on the securing band 250 of FIG. 1 to pass through and engage the FPCB 210 when inserted into the fastening holes 232 formed in the housing 230.

Both sides of the through-hole 213 are provided with a plurality of electrified holes 212 to which the power lines 214 of the + electrode and the power lines 214 of the − electrode are connected, respectively, and the electrified holes 212 are formed by a pair of + and − electrodes spaced apart from each other with respect to the through-hole 213.

In this case, the power lines 214 of the + electrode are connected to the through-hole 213 formed on one side of the through-hole 213, and the power lines 214 of the − electrode are connected to the through-hole 213 formed on the other side of the through-hole 213, so that the electrified holes 212 located on either side of the through-hole 213 can be fixed with either + or − poles.

Additionally, the FPCB 210 may be configured with a control circuit to receive a control signal from the main unit 100 through the control line 215 or to transmit the status of performing the electrical stimulation to the main unit 100, and to change the intensity, intensity, pattern, and position of the electrical stimulation based on the biometric information of the user determined from the main unit 100.

The fixture 220 is designed to encase the top of the pogo pins 211 formed on the FPCB 210, protecting them from external impacts. It also locks into the housing 230 when the FPCB 210 is inserted, preventing the FPCB 210 from detaching. Additionally, when the main unit 100 is connected to the FPCB 210, the fixture 220 ensures that the housing 230 remains securely attached to the main unit 100.

In essence, the fixture 220 is designed to fasten the FPCB 210 within the housing 230 and to secure the housing 230 to the main unit 100. The fastening mechanism can be a hook, snap fit, or screw connection.

The housing 230 features an opening on one side to allow the insertion of the FPCB 210. It is preferably made from an elastic synthetic resin material such as silicone or rubber. This material choice not only insulates against the effects of the electrodes but also minimizes the risk of inducing skin diseases upon contact with the skin.

The FPCB 210, which is inserted inside the housing 230, is also made of a flexible material that allows the substrate to bend, and the housing 230 is also formed of a synthetic resin material, which allows it to conform to the user's wrist.

The housing 230 features a connection hole 231 and a fastening hole 232, which align with the electrified holes 212 and the through hole 213 in the FPCB 210, exposing them to the exterior. This alignment allows the electrode end 420 on the stimulation portion 400 to contact the electrified holes 212 through the connection hole 231, enabling it to receive electricity.

The fastening holes 232 are designed to accommodate the fastening end 260 from the securing band 250 shown in FIG. 1. This fastening end 260 sequentially passes through the fastening holes 232 on the upper surface of the housing 230, the through-hole 213 in the FPCB 210, and the fastening holes 232 on the lower surface of the housing 230, where it then engages to secure the securing band 250 to the stimulation portion 200.

The other side of the housing 230 is also provided with a fastening loop 240 formed in the form of a ring into which the securing band 250 can be inserted, the fastening loop 240 being used to secure the left and right position of the securing band 250 when the fastening end 260 of the securing band 250 is inserted into the fastening hole 232.

The stimulation portion 400 contacts the skin on the user's wrist and administers low-frequency electrical stimulation to promote relaxation, reducing stress and excitability. Comprising a body 410 and an electrode end 420, the stimulation portion 400 also helps alleviate hypertension by electrically stimulating the median and ulnar nerves located beneath the Neiguan (PC6) and JianShi (PC5) acupoints.

The body 410 is made from a silicone ring that allows it to move along the outer surface of the housing 230 while insulating against electrical conduction. The electrode ends 420 are constructed as two separate components on the lower surface of the body 410.

Here, the two electrode ends 420 are formed to receive power by contacting the + and – poles of the electrified holes 212 formed on the FPCB 210, respectively, and based on the power received, the user's wrist can be electrically stimulated.

To facilitate the insertion of the electrode ends 420 through the connection holes 231 in the housing 230 to the electrified holes 212 on the FPCB 210, the electrode ends 420 are designed with one end elongated towards the interior of the body 410. The other end is shaped in a flattened form to prevent a foreign sensation when contacting the user's wrist.

The other end of the electrode ends 420 that contact the user's wrist is preferably protruding higher than the surface of the body 410 because if it is aligned with the lower surface of the body 410, the electrode ends 420 may not make contact with the skin of the wrist and no electrical stimulation may be applied.

When the electrode ends 420 are connected to the electrified holes 212, the electrode end 420 formed on one side are connected to the power line 214 of the + electrode, and the electrode end 420 formed on the other side is connected to the power line 214 of the electrode.

This configuration ensures that the two electrode ends 420, each connected to different electrodes on opposite sides, contact the user's wrist when energized. An electrical stimulus is then applied as current flows between these two electrode ends 420.

Figure 7:
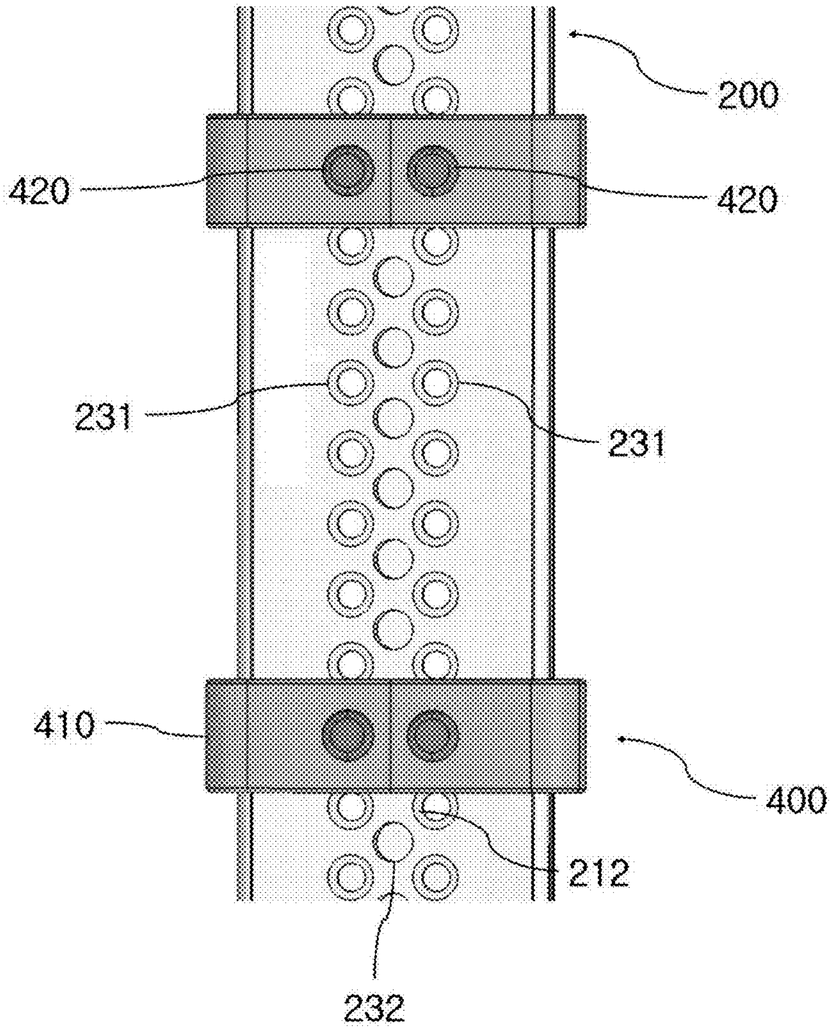
FIG. 7 is a bottom perspective view of the stimulation portion of a smart wearable wristband, with electrical electrodes for non-invasive neurostimulation, coupled to a stimulation band, as per the present invention.

FIG. 7 is a bottom perspective view illustrating a stimulation portion 400 of a smart wearable wristband with electrical electrodes for non-invasive neurostimulation coupled to a stimulation band 200 in accordance with the present invention.

As shown in FIG. 7, a stimulation portion 400 of a smart wearable wristband with electrical electrodes for non-invasive neurostimulation according to the present invention is characterized in that the stimulation portion 400 is formed to slide along the stimulation band 200 so that the neurostimulation portion can be adjusted.

The stimulation portion 400 is also characterized in that it is formed in a plurality to allow simultaneous stimulation at various locations on the wrist.

Because the stimulation portion 400 is ring-shaped, it can be freely moved along the outer surface of the stimulation band 200, allowing the stimulation portion 400 to be moved to the point or nerve location that needs to be stimulated and then electrically stimulated.

Since the stimulation portion 400 must be in communication with the stimulation band 200 to be powered, its range of movement is limited to the location of the connection hole 231 formed in the stimulation band 200, but there are substantially multiple electrified holes 212 from one end of the stimulation band 200 to the other end, so it can be moved to various locations to apply electrical stimulation.

The stimulation portion 400 can also be formed into multiple stimulation bands 200 to simultaneously apply electrical stimulation to various parts of the body according to the user's biometric information, thereby realizing the same effect as acupuncture points on various parts of the body from a Chinese medicine perspective.

When multiple stimulation portions 400 are formed, the FPCB 210 inside the stimulation band 200 may be formed to individually control the power supplied to each electrified hole 212, and such control may allow multiple stimulation portions 400 to be sequentially electrically stimulated according to symptoms.

Moreover, since the insertion points of the electrode ends 420 are determined by the electrified holes 212, the main unit 100 can also provide location information to the user. This enables targeting specific points for neurostimulation based on the biometric information gathered.

As discussed, a smart wearable wristband featuring an electrical electrode for non-invasive neurostimulation, as per this invention, can alleviate symptoms or conditions by applying electrical stimulation based on stress levels and excitability measured through biosignal monitoring. The device allows for the modification and adjustment of the electrical stimulation applied to the wrist. This enables the stimulation of various acupuncture points from the perspective of Chinese medicine. Additionally, its portability and integrated electrical stimulation module allow for easy application of stimulation outdoors, thereby helping to stabilize the user's vital signs.

Figure 8:
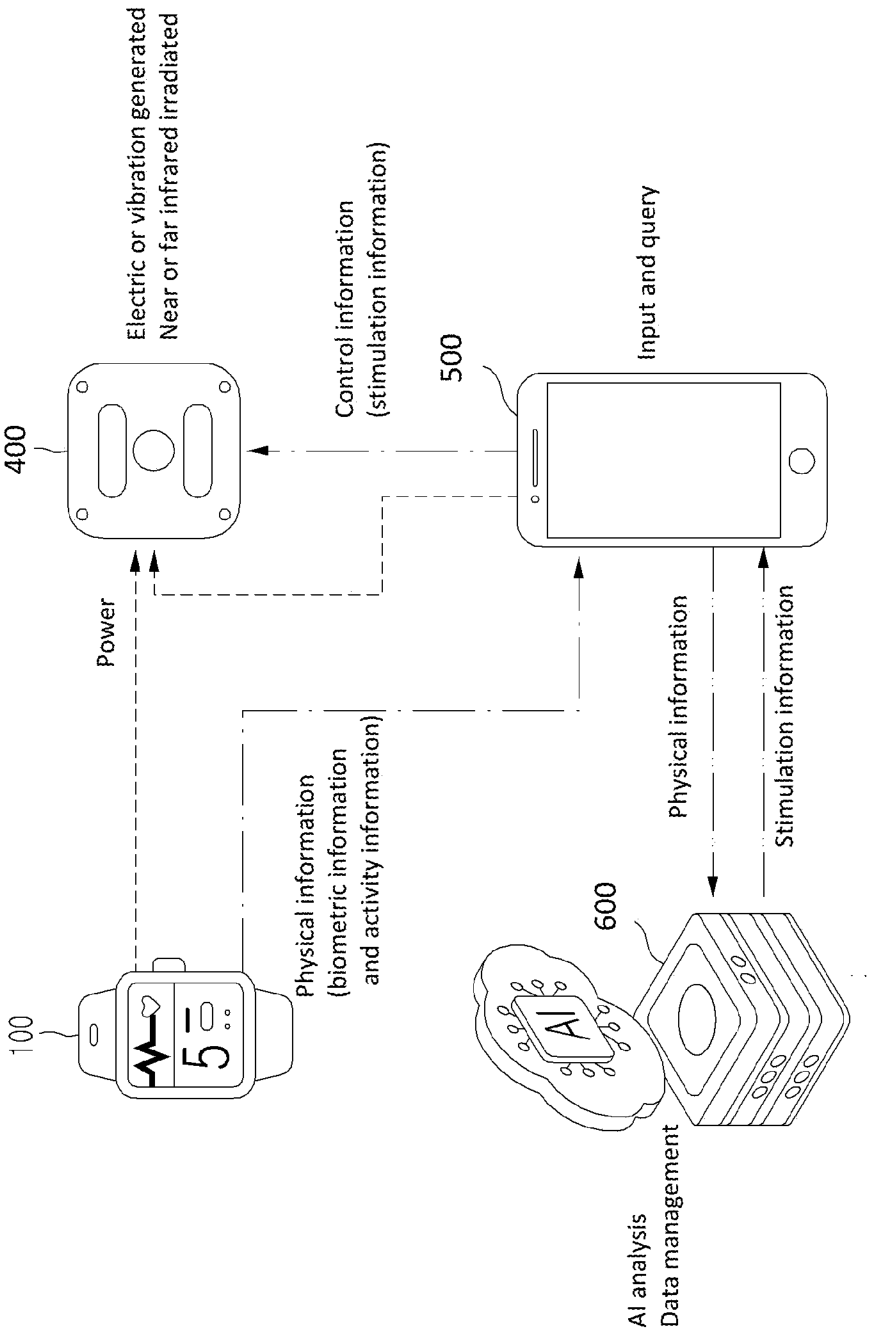
FIG. 8 is a conceptual diagram illustrating a non-invasive hypertension relief system according to another embodiment of the present invention.

Referring now to FIGS. 8 through 11, a detailed description follows of a non-invasive hypertension and stress relief system according to another embodiment of this invention. FIG. 8 provides a conceptual diagram of this system, illustrating one embodiment of the present invention.

Referring to FIG. 8, a non-invasive hypertension relief system according to another embodiment of the present invention includes a user terminal 500, a hypertension and stress reliever 440, and an AI analysis server 600.

The user terminal 500 transmits the user's physical information to the AI analysis server 600.

More specifically, the user terminal 500 communicates wirelessly (LTE/Wi-Fi/BLE, etc.) with the main unit 100 of wearable device to receive physical information transmitted from the wearable device.

Here, the physical information may include biometric information (vital signs) and activity information about the user. Specifically, the biometric information may include at least one of blood pressure, oxygen saturation, respiration, pulse, body temperature, and blood glucose. Further, the activity information includes at least one of falls, sleep, steps, activity time, GPS location information, and three-dimensional inertial location information.

Figure 9:
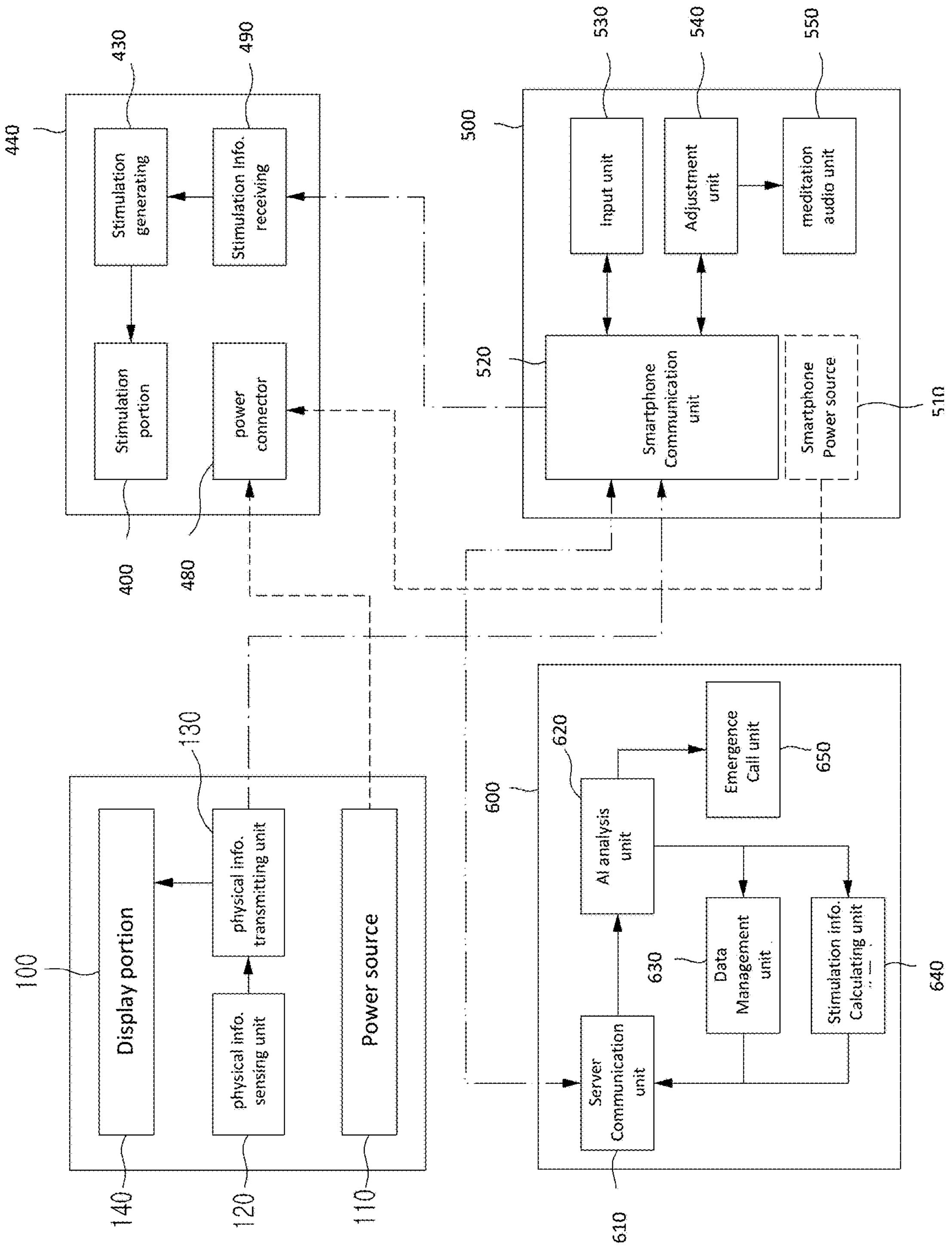
FIG. 9 is a block diagram illustrating a non-invasive hypertension relief system, according to another embodiment of the present invention.

FIG. 9 is a block diagram illustrating a non-invasive hypertension relief system according to one embodiment of the present invention.

In this embodiment, the user terminal 500 may be a smartphone, but is not limited thereto, and may be any wirelessly communicable electronic device, such as a tablet PC, MP3 player, or the like.

As shown in FIG. 9, the user terminal 500 includes a smartphone power unit 510, a smartphone communication unit 520, an input unit 530, an adjustment unit 540, and a meditation audio unit 550.

The smartphone power unit 510 provides power to the power connector 480 when electrically coupled to the power connector 480. The power connector 480 may also receive power from the main unit 100 of wearable device.

The smartphone communication unit 520 maintains wireless communication (LTE/Wi-Fi/BLE, etc.) with the main unit 100, the hypertension and stress reliever 440, and the AI analysis server 600, and is specifically designed to transmit and receive information. Additionally, this unit is electrically connected to both the input unit 530 and the adjustment unit 540, and it forwards physical data from the wearable device to the AI analysis server 600.

Further, the smartphone communication unit 520 may receive Stimulation information transmitted from the AI analysis server 600. The stimulation information may include at least one of a stimulation waveform, a operation mode, a stimulation time, a vibration mode, a near-infrared irradiation mode, and a far-infrared irradiation mode.

Specifically, the stimulation waveforms can include: an R-wave (square wave) based at 13 Hz, ranging from 10 Hz to 100 Hz, known for its strong energy intensity and its vibratory stimulation effect on acupuncture points; a P-wave (triangle wave) based at 3 Hz, ranging from 3 Hz to 20 Hz, which has a lower energy intensity but a potent stimulation effect on acupuncture points; and an S-wave (sine wave) based at 20 Hz, ranging from 5 Hz to 100 Hz, which provides gentle stimulation and massages the areas around acupuncture points.

Additionally, the intensity of all stimulus waveforms can be adjusted in 10 steps, ranging from 2 mA to 13 mA, based on a human body resistance of 500Ω. Furthermore, the default intensity settings for each stimulus waveform are 1× for the P-wave, 2× for the R-wave, and 3× for the S-wave.

There are three modes of operation: sequential mode, which applies the stimulus waveform to the electrodes in rotation, fixed mode, which fixes the stimulus waveform for each electrode, and single mode, which applies the same stimulus waveform to all electrodes.

Specifically, sequential mode applies different stimulus waveforms to multiple electrode pairs and alters the stimulus waveform at time intervals shorter than the period of the lowest frequency among the multiple stimulus waveforms.

In addition, the fixed mode applies different stimulus waveforms to multiple electrode pairs and the stimulus waveform does not change while the multiple electrode pairs are activated.

On the other hand, the single mode applies the same stimulus waveform to multiple electrode pairs.

If the control unit 540 automatically controls the Stimulation information, the smartphone communication unit 520 transmits the Stimulation information to the hypertension and stress reliever 440.

The input unit 530 enables manual input of physical information by the user, and enables inquiry of body analysis information, blood pressure history information, and stimulation information.

Specifically, the input unit 530 can manually input physical information through the user's operation and retrieve physical information managed by the AI analysis server 600 and stimulation information analyzed by the AI analysis server 600.

Accordingly, the input unit 530 is electrically connected to the smartphone communication unit 520.

The adjustment unit 540 automatically or manually controls the Stimulation information transmitted from the smartphone communication unit 520 and transmits it to a smartphone receiving unit provided in the smartphone communication unit 520.

First, when the adjustment unit 540 automatically controls the Stimulation information, the adjustment unit 540 transmits the automatically controlled Stimulation information to the smartphone communication unit 520.

On the other hand, when the adjustment unit 540 manually controls the Stimulation information, the adjustment unit 540 adjusts the Stimulation information transmitted from the AI analysis server 600 and transmits the adjusted Stimulation information to the hypertension and stress reliever 440 while simultaneously operating the meditation audio unit 250. The adjustment unit 540 is electrically connected to the smartphone communication unit 520 and the meditation audio unit 550. The meditation audio unit 550 generates one of meditation music, meditation sounds, and white noise.

Figure 10A:
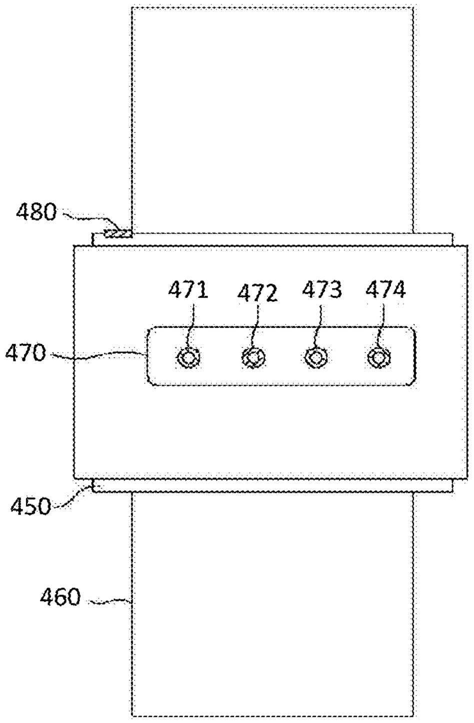
FIGS. 10A and 10B are top and bottom views illustrating a detailed configuration of a Hypertension and stress reliever in a non-invasive hypertension relief system, as per another embodiment of the present invention.
Figure 10B:
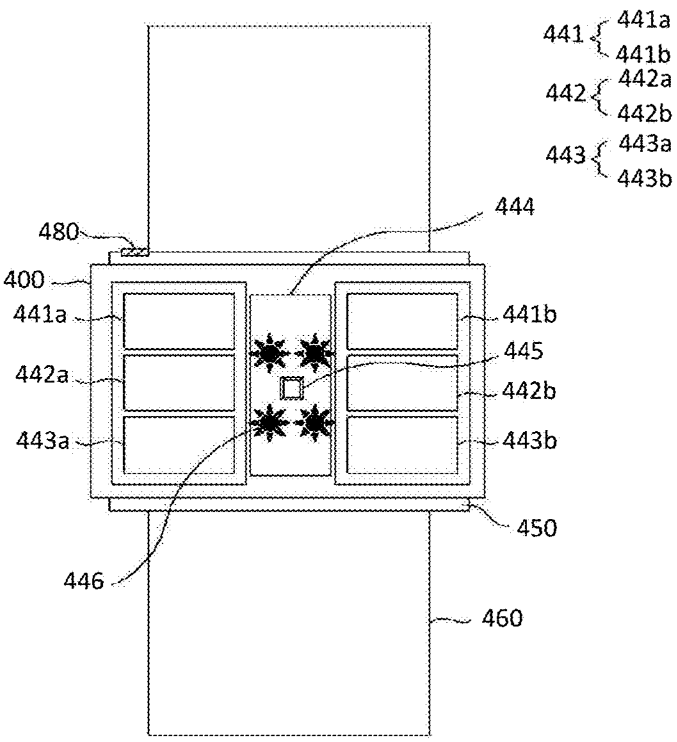

FIGS. 10A and 10B are top and bottom views illustrating a detailed configuration of a hypertension and stress reliever 440 in a non-invasive hypertension and stress relief system according to another embodiment of the present invention.

The hypertension and stress reliever 440, worn on at least part of the user's body, delivers one or more types of stimulation-electrical, vibrational, or light-to at least part of the user's body. This is in response to stimulation information received from the AI analysis server 600.

Here, photostimulation includes light irradiation using far infrared light and light irradiation using near infrared light.

For this purpose, the hypertension and stress reliever 440 may communicate wirelessly (LTE/Wi-Fi/BLE, etc.) with user terminal 500 or main unit 100 of the wearable device to the AI analysis server 600.

Additionally, a hole is formed in the center of the hypertension and stress reliever 440 for passing near-infrared light from the near-infrared LED 446, as shown in FIG. 10B.

Referring to FIGS. 9, 10A, and 10B, the hypertension and stress reliever 440 may include a power connector 480, a stimulation information receiving portion 490, a stimulation generating portion 430, a stimulation portion 400, a strap connector 450, a strap 460, and an LED indicator 470.

The power connector 480 is electrically connected to either the wearable device or the user terminal 500, serving as a connector. However, the hypertension and stress relief device 440 may not include the power connector 480 and could instead be equipped with a battery.

The power connector 480 is coupled to the strap connector 450, as shown in FIGS. 10A and 10B.

Referring to FIG. 9, the stimulation information receiving portion 490 is in wireless communication (LTE/Wi-Fi/BLE, etc.) with the smartphone communication unit 520.

Accordingly, the stimulation information receiving portion 490 receives automatically or manually controlled Stimulation information transmitted from the smartphone communication unit 520.

Referring to FIG. 9, the stimulation generating portion 430 is electrically connected to the stimulation information receiving portion 490 to generate a stimulus waveform in response to control Stimulation information transmitted from the Stimulation information receiving portion 490.

Referring to FIGS. 9 and 10A and 10B, the stimulation portion 400 is coupled to the strap connector 450 and can provide electrical stimulation, vibration stimulation, or light stimulation to at least a portion of the user's arm based on stimulation information. Here, the light stimulation includes light irradiation using far infrared and near infrared light.

Referring to FIG. 10B, the stimulation portion 400 includes a first electrode 441, a second electrode 442, a third electrode 443, a silicone pad 444, a vibration stimulation terminal 445, and a near-infrared LED 446. The first electrode 441 is designed to transmit a stimulus waveform from the stimulation generator 430 to electrically stimulate the median or ulnar nerve located beneath the Neiguan PC 6 or Jianshi PC 5 acupoints between the user's wrist and forearm, and includes a pair of sub-electrodes 441*a* and 441*b*.

The pair of first electrodes 441*a*, 441*b* are disposed to be spaced a predetermined distance apart from each other, and between the pair of first electrodes 341 is the top of the silicone pad 444.

Additionally, a second electrode 442 may be positioned on one side of the pair of first electrodes 441 and may deliver a stimulus waveform from the stimulation generating portion 430 to electrically stimulate the median nerve or ulnar nerve beneath the JianShi PC 5 or the Neiguan PC 6, and may include a pair of electrodes 442*a*, 442*b*.

The pair of second electrodes 442*a*, 442*b* are arranged to be spaced a predetermined distance apart from each other, and between the pair of second electrodes 442 is the center portion of the silicone pad 444.

A third electrode 443, located ipsilaterally to the pair of second electrodes 442*a* and 442*b*, includes a pair of sub-electrodes 443*a* and 443*b*. This setup allows it to deliver a stimulus waveform from the stimulation generator 430, which can electrically stimulate the median or ulnar nerve beneath the Jianshi PC 5 or Neiguan PC 6 acupoints.

The pair of third electrodes 443*a*, 443*b* are arranged to be spaced apart from each other by a predetermined distance, and between the pair of third electrodes 443*a*, 443*b* is positioned the lower portion of the silicone pad 444.

The silicone pads 444 are positioned between the pairs of first electrodes 441, second electrodes 442, and third electrodes 443, and are also located adjacent to the near-infrared LEDs 446.

The silicone pad 444 is heated by a heat source including a near-infrared LED 446 according to the stimulation information transmitted from the Stimulation information receiving portion 490 to generate far-infrared radiation, and then the generated far-infrared radiation is irradiated to the user's blood vessels.

The vibration stimulation terminal 445 is coupled to the bottom center of the silicone pad 444, and generates vibration stimulation according to the stimulation information transmitted from the stimulation information receiving portion 490, and then uses the generated vibration stimulation to vibrationally stimulate the user's median nerve.

The near-infrared LED 446 is attached to the back surface of the silicone pad 444. Specifically, it generates near-infrared light based on the stimulation data received from the stimulation information receiving unit 490, and emits this light into the user's blood vessels.

The unit consists of multiple LEDs. In this particular invention, the near-infrared LED 446 includes four LEDs, although the number is not limited to four.

The strap connector 450 may be formed from a flat plate having a predetermined thickness. Each side of the strap connector 450 may have a strap 460 coupled to it, and one of the two sides of the strap connector 450 may have a power connector 480 coupled to it. In this case, the straps 460 may be configured in pairs such that they may each be coupled to both sides of the strap connector 450.

Figure 11:
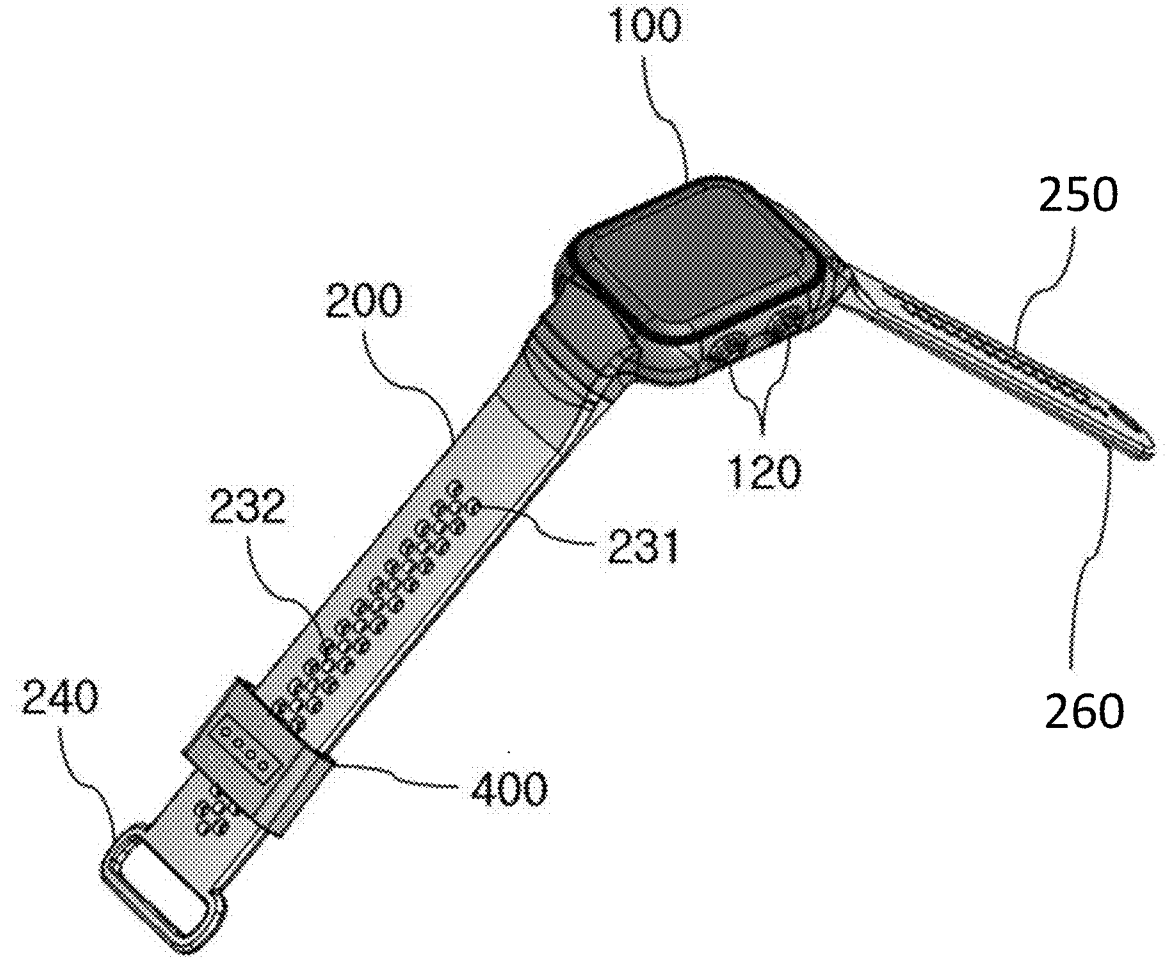
FIG. 11 is a perspective view illustrating the appearance of a smart wearable wristband with electrical electrodes for non-invasive neurostimulation, according to another embodiment of the present invention.

Alternatively, the power connector 480 may be coupled to the strap connector 450 via a wire inside the strap 460 from the wearable device in a structure similar to the structure of FIG. 1, for example, as shown in FIG. 11.

The LED indicator 470 indicates on and off based on the operation of the power connector 480, the plurality of near-infrared LEDs 446, the pair of first and third electrodes 441, 442, 443, and the vibration stimulation terminal 445.

Referring to FIG. 10A, the LED display 470 may include a power indicator LED 471, a near-infrared motion indicator LED 472, a stimulation indicator LED 473, and a vibration indicator LED 474.

The power indicator LED 471 is electrically coupled to the power connector 480 to illuminate in response to operation of the power connector 480.

Specifically, the power indicator LED 471 lights up when either the power source 110 or the smartphone power source 510 is electrically connected to and powering the power connector 480, and it turns off when the power connector 480 is disconnected or de-energized.

The near-infrared motion indicator LED 472 is electrically coupled to the plurality of near-infrared LEDs 446 to emit light in response to the motion of the plurality of near-infrared LEDs 446.

Specifically, the near-infrared motion indicator LED 472 illuminates when a plurality of the near-infrared LEDs 446 are actuated, while the near-infrared LEDs 446 are dimmed when a plurality of the near-infrared LEDs 446 are not actuated.

The stimulation indicator LED 473 is electrically coupled to the pair of first and third electrodes 441, 442, 443 to illuminate in response to the behavior of the pair of first and third electrodes 441, 442, 443.

Specifically, the stimulation indicator LED 473 is illuminated when the pair of first and third electrodes 441, 442, 443 is actuated, but is extinguished when the pair of first and third electrodes 441, 442, 443 is not actuated.

The vibration indicator LED 474 is electrically coupled to the vibration stimulation terminal 445 to illuminate in response to motion of the vibration stimulation terminal 445.

Specifically, the vibration indicator LED 474 illuminates when the vibration stimulation terminal 445 is actuated, but turns off when the vibration stimulation terminal 445 is not actuated.

As shown in FIG. 8, the AI analysis server 600 analyzes the physical information transmitted from the user terminal 500 to generate physical analysis information and blood pressure history information, calculates Stimulation information according to the physical analysis information and blood pressure history information, and transmits the Stimulation information to the user terminal 500.

More specifically, referring to FIG. 9, the AI analysis server 600 includes a server communication unit 610, an AI analysis unit 620, a data management unit 630, a stimulation information calculation unit 640, and an emergency call unit 650.

The server communication unit 610 receives the physical information transmitted from the smartphone communication unit 520. The server communication unit 610 also transmits the stimulation information transmitted from the stimulation information calculation part 400 to the smartphone communication unit 520.

The AI analysis unit 620 analyzes the physical information transmitted from the server communication unit 610 to generate physical analysis information and blood pressure history information, and determines whether there is an emergency by comparing the preset physical analysis information with the physical analysis information and comparing the preset blood pressure history information with the blood pressure history information.

The data management unit 630 stores and manages the body analysis information and blood pressure history information transmitted from the AI analysis unit 620.

The Stimulation information calculation unit 640 calculates the Stimulation information according to the body analysis information and blood pressure history information transmitted from the AI analysis unit 620.

The emergency call unit 650 receives the emergency signal transmitted by the AI analysis unit 420 and sends an emergency message to the nearby hospital, the 911 safety center, and the user terminal held by the user's guardian, respectively.

The present invention may further include a wearable device that is worn on a user's body to collect physical information about the user.

Specifically, main unit 100 of the wearable device transmits Physical information to the user terminal 500.

In the present invention, the wearable device may exemplarily be a smartwatch, but is not limited thereto.

The main unit 100 of the wearable device includes a power source 110, a physical information sensing unit 120, a physical information transmitting unit 130, and a display portion 140.

The power source 110, when connected to the hypertension and stress reliever 440, can supply power to the hypertension and stress reliever 440 via the power connector 480.

The physical information sensing unit 120 collects the Physical information generated after detecting the body signals of the user.

The physical information transmitting unit 130 is electrically connected to the physical information sensing unit 120 and receives the biometric information transmitted from the physical information sensing unit 120 and transmits it to the display portion 140. The display portion 140 displays the physical information transmitted from the physical information transmitting unit 130.

According to the above, the present invention has the advantage of effectively relieving hypertension or stress without medication through acupressure on the median nerve with a vibration stimulation terminal or R wave (square wave) and vibration stimulation, irradiation with near infrared and far infrared light, and meditative music provided by meditation audio.

While the invention has been described above with reference to a preferred embodiment, it will be apparent to one having ordinary skill in the art to which the invention belongs that many modifications or variations may be made to the invention without departing from the technical ideas and scope of the claims of the patent. The scope of the invention is therefore to be construed by the claims as written to include examples of many such variations.

What is claimed is:

1. A smart wearable wristband for non-invasive neurostimulation, comprising:

a main unit configured to fit around a wrist and measure a user's vital signs;

a stimulation portion configured to stimulate a median nerve or an ulnar nerve located below a Neiguan PC 6 or a JianShi PC 5;

a stimulation band formed at one end of the main unit, electrically connected to the main unit to receive power, and including a fixing ring at the other end of the stimulation band; and a retaining band formed on another end of the main unit, configured to be coupled to the stimulation band via a fastening end, and configured to secure the main unit and the stimulation band to the user's wrist, wherein the stimulation portion is positioned on an outer surface of the stimulation band and is configured to receive power from the stimulation band, and wherein the stimulation band comprises a flexible printed circuit board (FPCB), and the FPCB is configured to bend to conform to the wrist, and the stimulation portion is configured to control intensity and timing of stimulation based on the vital signs.

2. The smart wearable wristband of claim 1, wherein the stimulation portion comprises:

a body formed to wrap around the stimulation band, the body being configured to slide along the stimulation band; and electrode ends formed on a lower surface of the body, the electrode ends configured to be electrically connected to supply positive and negative charge when inserted into said stimulation band and establishing contact with the wrist to provide electrical stimulation.

3. The smart wearable wristband of claim 1, wherein the stimulation portion is configured to slidably move along said stimulation band to adjust a neurostimulation portion.

4. A smart wearable wristband for non-invasive neurostimulation, comprising:

a main unit configured to fit around a wrist and measure a user's vital signs;

a stimulation portion configured to stimulate a median nerve or an ulnar nerve located below a Neiguan PC 6 or a JianShi PC 5;

a stimulation band formed at one end of the main unit, electrically connected to the main unit to receive power, and including a fixing ring at the other end of the stimulation band; and a retaining band formed on another end of the main unit, configured to be coupled to the stimulation band via a fastening end, and configured to secure the main unit and the stimulation band to the user's wrist, wherein the stimulation portion is positioned on an outer surface of the stimulation band and is configured to receive power from the stimulation band, wherein the stimulation band comprises:

a flexible printed circuit board (FPCB) including a pogo pin at one end of the FPCB, electrified holes to supply power to the stimulation portion, and through-holes formed at a predetermined interval for insertion of the fastening end;

a fixture configured to protect the pogo pin by being wrapped around the pogo pin, and engaging with the main unit to prevent separation; and a housing accommodating the FPCB and having connection holes and fastening holes formed at the predetermined interval at the same locations as the through-holes and allowing the electrified holes to be exposed for connection with the stimulation portion, wherein the stimulation portion is configured to be coupled to the connection holes and the electrified holes on the stimulation band, allowing a stimulation position to be changed.

5. The smart wearable wristband of claim 4, wherein a plurality of stimulation portions are provided for simultaneous stimulation at multiple locations on the wrist.

6. A non-invasive hypertension or stress relief system comprising:

a user terminal;

an artificial intelligence (AI) analysis server;

a hypertension and stress reliever; and a wearable device configured to be worn by a user to collect physical information about the user, wherein the user terminal configured to transmit the physical information to the AI analysis server, and the AI analysis server configured to generate physical analysis data based on the user's physical information and a blood pressure history; configured to calculate stimulation information based on the physical analysis; and configured to transmit the stimulation information to the user terminal;

wherein the hypertension and stress reliever is configured to provide electrical stimulation in accordance with the stimulation information and to stimulate a median nerve or an ulnar nerve below a Neiguan PC 6 or a JianShi PC 5;

wherein the user terminal comprises:

a smartphone communication unit configured to communicate with the wearable device, the hypertension and stress reliever, and the AI analysis server, transmit the physical information to the AI analysis server and receive the stimulation information;

an input unit configured to allow manual input of physical information by the user, and query of the physical analysis data, the blood pressure history, and the stimulation information; and an adjustment unit configured to control the transmission of the stimulation information from the smartphone communication unit to a smartphone receiver and a smartphone transmitter and configured to send the stimulation information to the hypertension and stress reliever.

7. The non-invasive hypertension or stress relief system of claim 6, wherein the hypertension and stress reliever is configured to further provide vibration stimulation or light stimulation in accordance with the stimulation information.

8. The non-invasive hypertension or stress relief system of claim 6, wherein the AI analysis server comprises:

a server communication unit configured to wirelessly communicate with the smartphone communication unit to receive physical information;

an artificial intelligence (AI) analysis unit configured to analyze the physical information to generate physical analysis information and blood pressure history, compare preset analysis information with the received information, and determine if there is an emergency;

a data management unit configured to store and manage the physical analysis information and blood pressure history; and a stimulation information calculation unit configured to calculate the stimulation information based on the physical analysis and blood pressure history, wherein the server communication unit is configured to transmit the stimulation information to the smartphone communication unit.

9. The non-invasive hypertension or stress relief system of claim 8, wherein the hypertension and stress reliever includes:

a strap connector;

a pair of straps attached to either side of said strap connector;

a stimulation information receiving unit configured to receive the stimulation information from the smartphone communication unit;

a stimulation generating unit configured to generate an electrical stimulation waveform based on the stimulation information; and a stimulation portion coupled to said strap connector to provide electrical, vibration, and light stimulation to at least a part of the user's arm according to the stimulation information.

10. The non-invasive hypertension or stress relief system of claim 9, further comprising a plurality of near-infrared LEDs configured to generate near-infrared light according to the stimulation information and irradiate said light into the user's blood vessels.

11. The non-invasive hypertension or stress relief system of claim 10, further comprising a silicone pad disposed adjacent to the plurality of near-infrared LEDs, configured to generate far-infrared light by heating and irradiate the far-infrared light into user's blood vessels.

* * * * *